(12) United States Patent
Hammond et al.

(10) Patent No.: US 6,195,443 B1
(45) Date of Patent: *Feb. 27, 2001

(54) SYSTEM USING ON-LINE LIQUID CHARACTERIZATION APPARATUS

(75) Inventors: John M. Hammond, Ontario; Jian Cai, Penfield; Kent J. Evans, Lima; John G. Matta, Rochester; Robert F. Dunham, Walworth; Mario Errico, Fairport; Julie A. Cady, Rochester; Mark C. Petropoulos, Ontario; Stanley J. Pietrzykowski, Jr., Rochester; Mark S. Thomas, Williamson, all of NY (US)

(73) Assignee: Xerox Corporation, Stamford, CT (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/079,791

(22) Filed: May 15, 1998

(51) Int. Cl.$^7$ ............................... A61B 5/00; G06K 9/00
(52) U.S. Cl. .................... 382/100; 382/128; 382/134; 364/528; 356/73
(58) Field of Search ..................... 382/100, 110; 356/128, 301, 208, 442, 73; 264/401, 184; 241/91; 364/528; 600/310; 436/164; 700/273

(56) References Cited

U.S. PATENT DOCUMENTS

| | | | |
|---|---|---|---|
| 3,838,926 | * 10/1974 | Kato et al. | 356/208 |
| 5,521,699 | 5/1996 | Kosaka et al. | 356/73 |
| 5,573,721 | * 8/1999 | Gillette | 264/401 |
| 5,715,047 | * 2/1998 | Adamosky | 356/128 |
| 5,786,893 | * 7/1998 | Fink et al. | 356/301 |
| 5,841,884 | * 11/1998 | Yamamoto | 382/110 |
| 5,946,220 | * 8/1999 | Lemelson | 364/528 |
| 5,983,120 | * 11/1999 | Groner et al. | 600/310 |

OTHER PUBLICATIONS

*An Introduction to Fluid Dynamics* by G.K. Batchelor (Cambridge University Press, 1967)(copies of the title page, pp. 222–223 and 604–605 are attached).

* cited by examiner

*Primary Examiner*—Matthew C. Bella
*Assistant Examiner*—M Choobin
(74) *Attorney, Agent, or Firm*—Zosan S. Soong

(57) ABSTRACT

A manufacturing system including: (a) a vessel for holding a liquid; (b) a first member and a second member, each having a flat surface, wherein the flat surface of the first member faces and is spaced from the flat surface of the second member, thereby defining a gap region between the two flat surfaces, wherein a section of the first member is transparent through the thickness of the first member; (c) a liquid delivery system connected to the vessel and the gap region which delivers the liquid to the gap region and the liquid flows in the gap region in view of the transparent section of the first member; (d) a camera positioned to view through the transparent section of the first member; (e) image processing means coupled to the camera for determining the homogeneity of the liquid in the gap region; and (f) liquid dispensing equipment connected to the liquid delivery system.

10 Claims, 6 Drawing Sheets

US 6,195,443 B1

SYSTEM USING ON-LINE LIQUID CHARACTERIZATION APPARATUS

FIELD OF THE INVENTION

This invention relates to a manufacturing system using on-line apparatus for determining the homogeneity of a liquid.

BACKGROUND OF THE INVENTION

An organic solvent, a binder resin, and a pigment are combined and milled for use in the charge generation layer in the fabrication of organic photoreceptors. The pigment and binder resin are chosen to optimize their photoelectric properties, but it is not always possible to optimize the dispersion quality of the resulting coating solution. Charge generating solutions that become unstable over time are a common problem in the fabrication of certain organic photoreceptors. Unstable dispersions result in coating defects in the charge generating layer that lower coating yield during the fabrication process. There is a need, which the present invention addresses, for a manufacturing system that can continuously monitor the dispersion quality of the charge generating solution to be able to prevent coating defects by replacing the charge generating solution on the onset of loss of dispersion quality.

One device that may be effectively used as a tool to monitor dispersion quality is a Hele Shaw flow cell. A Hele Shaw flow cell comprises a pair of flat plates narrowly separated from each other by a fixed distance, and held parallel to each other, thereby creating a gap region between the two plates. The Hele Shaw cell is typically dimensioned such that the separation distance between the plates is several orders of magnitude less than the remaining two orthogonal dimensions defined by the planar surface of either of the plates. A further description of the Hele Shaw flow cell may be found in An Introduction to Fluid Dynamics by G. K. Batchelor (Cambridge University Press, 1967) (copies of the title page, pages 222–223 and 604–605 are attached).

At times over the past several years, a number of the co-inventors checked the quality of a charge generating dispersion batch by taking a small sample from the batch to a laboratory located away from the photoreceptor fabrication line, and running the sample through a rectangular Hele Shaw flow cell where a human operator using a microscope viewed the sample flowing through the flow cell. The batch was approved or disapproved for use in Xerox commercial photoreceptors based on the dispersion quality results of the sample. The sample was then typically discarded. A problem with the above described procedure is that manually checking a sample at a laboratory separated from the photoreceptor fabrication line is very inefficient from a manufacturing viewpoint. The present invention addresses this problem.

A flow cytometer for investigating particle constituents in liquids is described in Kosaka et al., U.S. Pat. No. 5,521,699.

SUMMARY OF THE INVENTION

The present invention is accomplished in embodiments by providing a manufacturing system comprising:

(a) a vessel for holding a liquid;
(b) a first member and a second member, each having a flat surface, wherein the flat surface of the first member faces and is spaced from the flat surface of the second member, thereby defining a gap region between the two flat surfaces, wherein a section of the first member is transparent through the thickness of the first member;
(c) a liquid delivery system connected to the vessel and the gap region which delivers the liquid to the gap region and the liquid flows in the gap region in view of the transparent section of the first member;
(d) a camera positioned to view through the transparent section of the first member;
(e) image processing means coupled to the camera for determining the homogeneity of the liquid in the gap region; and
(f) liquid dispensing equipment connected to the liquid delivery system.

In the present invention, at least a portion of the charge generating dispersion is directed to flow through a Hele Shaw cell in the gap region, resulting in a thin, substantially two-dimensional flowing film. The present invention further includes means to evaluate the quality of the charge generating dispersion by observation and analysis of the appearance of the two dimensional flowing dispersion film.

BRIEF DESCRIPTION OF THE DRAWINGS

Other aspects of the present invention will become apparent as the following description proceeds and upon reference to the Figures which represent preferred embodiments.

Unless otherwise noted, the same reference numeral in different Figures refers to the same or similar feature.

DETAILED DESCRIPTION

Figure 1:
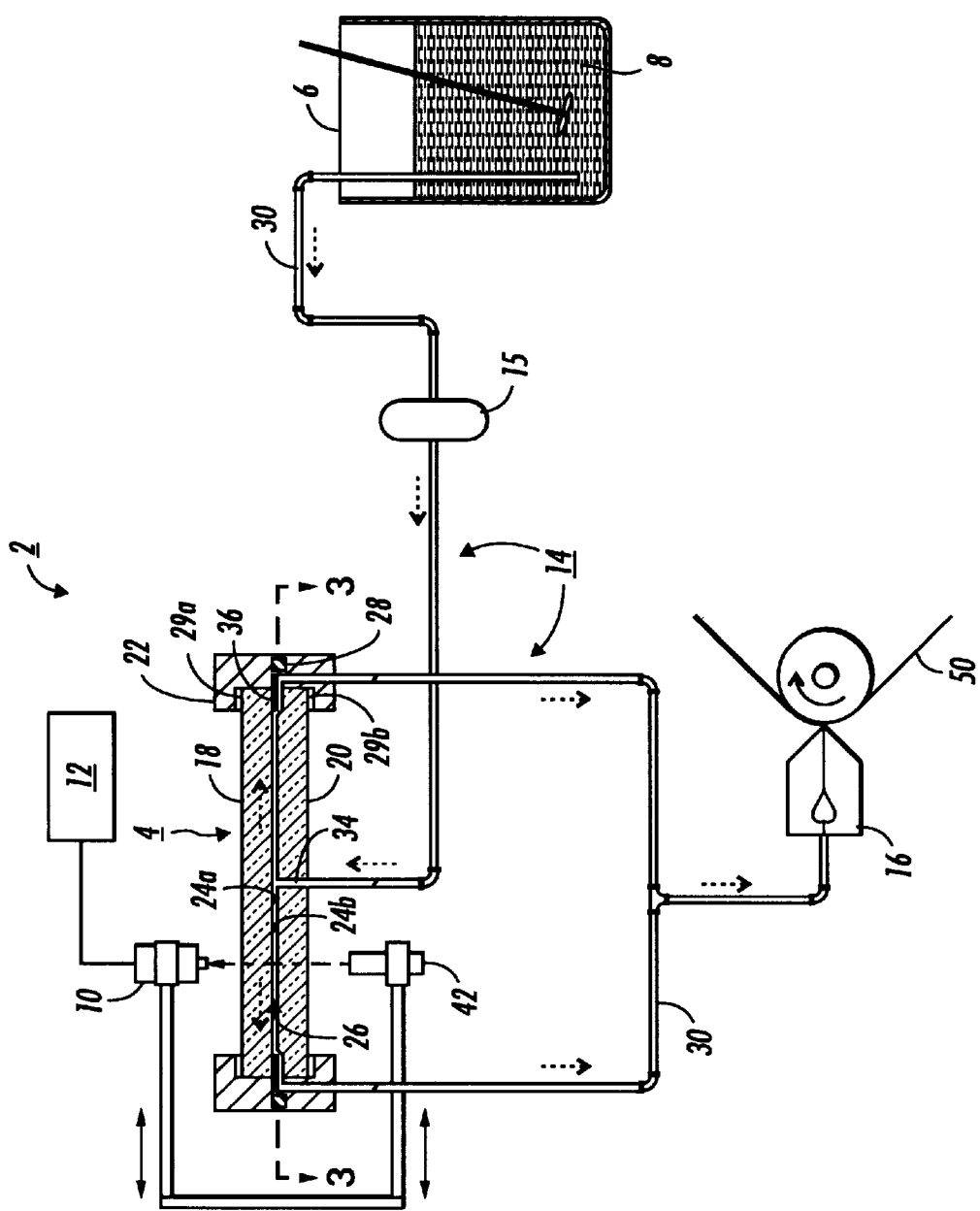
FIG. 1 is a simplified elevational drawing of one embodiment of the present manufacturing system.

In FIG. 1, the manufacturing system 2 is composed of a flow cell 4, a vessel 6 holding a liquid 8, a camera 10, image processing means 12, liquid delivery system 14, and liquid dispensing equipment 16.

The flow cell 4 is composed of a first member 18, a second member 20, and a housing 22 supporting the two members, each member having a flat surface (24a, 24b), wherein the two flat surfaces face one another and are spaced from each other by a shim 36 to define a gap region 26. It is preferred that the two flat surfaces (24a, 24b) are parallel to one another. A section of the first member 18 is transparent through the thickness of the first member. Preferably, the first member is transparent along its entire length and through the thickness of the first member, i.e., all of the first member is transparent. A section of the second member 20 may also be transparent. Preferably, the second member is transparent along its entire length and through the thickness of the second member, i.e., all of the second member is transparent. As used herein, the term transparent refers to the ability of a material to allow light to pass through the material with little or no diffusion and the intensity of the light is diminished after passage through the material by an amount ranging for example from 0% to about 70% compared with the light intensity prior to passage through the material; the extent of any diffusion should not significantly impair the perception of distinct images. One or more O-rings 28, and flat gaskets (29a, 29b) are provided at appropriate locations to prevent leakage of liquid from the flow cell. In embodiments, the first and second members could be provided with a transparent conductive coating such as indium tin oxide on their wetted surfaces. These resulting conductive surfaces could then be suitably connected to a voltage source so that the migration of for example charge generator pigment particles during flow through an applied electric field could be observed.

In FIGS. 1–4, the first member 18 and the second member 20 may be disk shaped plates with a diameter ranging for example from about 10 cm to about 40 cm. In embodiments, the two members are about 25 cm in diameter and have a thickness of about 2.5 cm. The first and second members may be fabricated by precision methods used in the production of optical flats, with the inner (wetted) surfaces being made flat to preferably within about one wavelength (about 632 nm). The two members may be made from a glass like material such as quartz or fused silica or a transparent plastic material that is resistant to the liquid.

Figure 3:
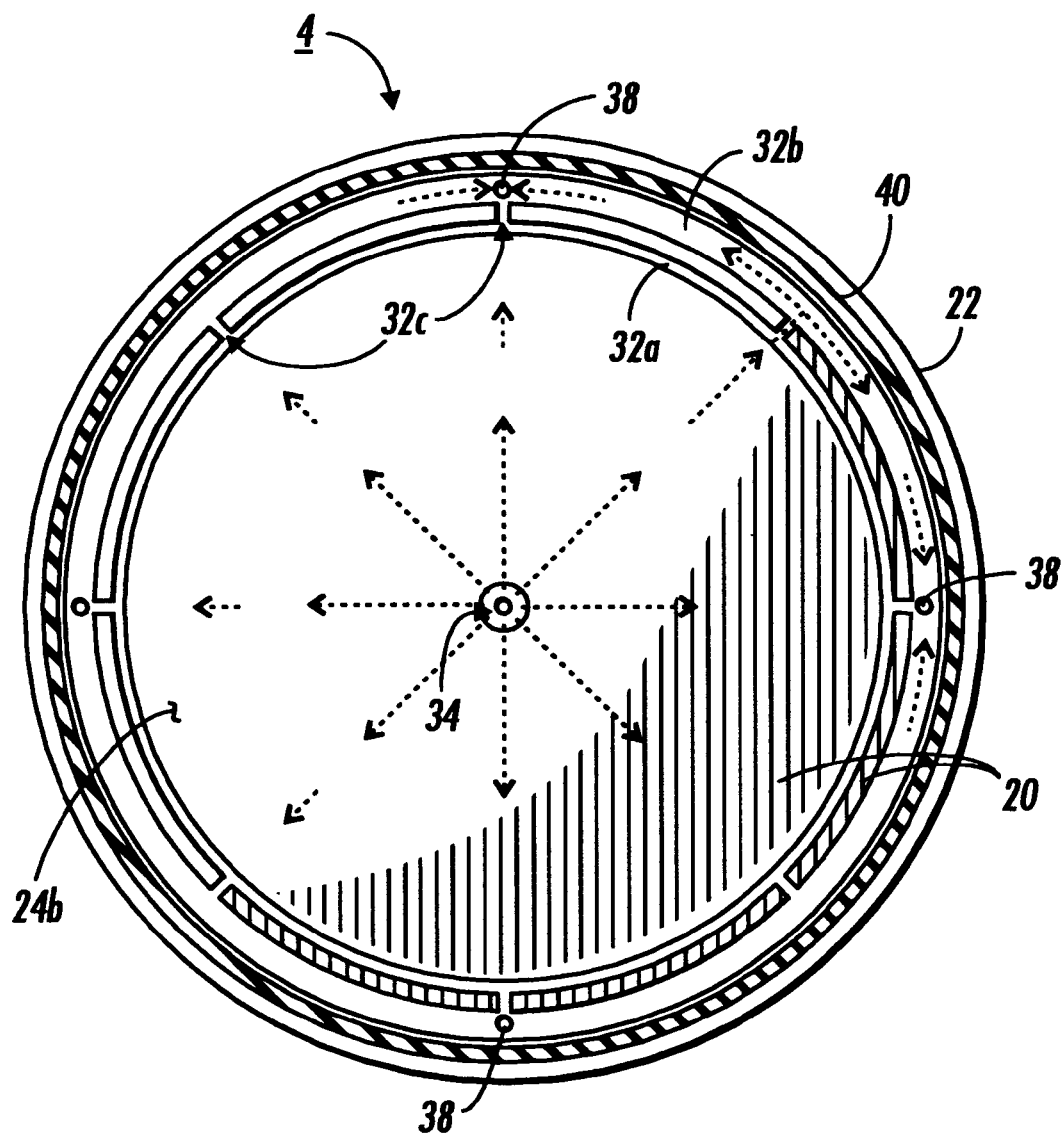
FIG. 3 is a simplified, plan view of the bottom half of the flow cell used in FIG. 1.

The liquid delivery system 14 includes tubing 30, liquid transport channels (32a, 32b, 32c) within the flow cell (e.g., channels, liquid outlet ports 38, and liquid inlet ports 34 within the housing and the first member and the second member), and one or more pumps 15 to deliver the liquid to the gap region 26 and to deliver the liquid to the liquid dispensing equipment. In embodiments of the present invention, the liquid delivery system includes a single liquid inlet port 34 positioned at the center of the gap region where the liquid flows in the gap region in for example a radial pattern. The liquid inlet port may be a strain relief TEFLON™ plug with a center port for liquid inlet. As seen in FIG. 3, there is depicted a channel 32a encircling and adjacent to the flat surface 24b for the outflow of liquid, and a circumferential channel 32b is connected to a series of radial channels 32c passing beneath the shim (channel 32b is in communication with channel 32a via radial channels 32c), thereby allowing the liquid to exit the flow cell via the outlet ports 38. There is also depicted in FIG. 3 a groove 40 in the housing for an O-ring. The first member 18 may have the same or similar configuration as the second member 20. Alternatively, the surface of the first member 18 facing the second member may be entirely flat without any channels or projecting areas.

A needle valve could be provided at the central fluid inlet port. The function of this needle valve would be to subject the liquid to extremely high shear immediately before it enters the flow cell, and subsequently flows through decreasing shear conditions out to the perimeter. This feature will help eliminate flocculation in dispersions by exceeding the dispersion yield point, which improves coating quality.

In embodiments, a liquid inlet port could be provided in the first member. This would enable a mode of operation in which two different liquids or even the same liquid can be supplied to the flow cell through both the first member and the second member. A flow separating disk located at the fluid inlet ports may be needed to stabilize the flow and prevent initial mixing of the two liquids.

The camera 10 is positioned to view through the transparent section of the first member. The camera may be a video camera, a high speed movie camera, a silver halide film still photography camera, a digital CCD still photography camera, and the like. Optionally, there may be a light source 42 disposed adjacent a transparent section of the second member to illuminate the liquid flow in the gap region.

The light source is preferably rated at between 10 and 1000 watts of power. The light source preferably produces substantially collimated light, with the size of the spot of light which illuminates the liquid flow preferably being a circular spot between 1 mm and 1 cm in diameter. The light source is chosen such that the particular charge generator dispersion that is being analyzed transmits a sufficient portion of the light to the camera to enable the generation of high quality images for analysis. Depending on the dispersion and gap thickness, the light source may be broad spectrum white light such as that obtained from a tungsten lamp; infrared light of 700 to 1000 nm wavelength; ultraviolet light of 250 to 400 nm wavelength; and the like.

The camera and the light source may be mounted together on a horizontal drive system and thus movable to traverse along the surface of the first member and the second member to better view the flow pattern of the liquid in the gap region. In embodiments, it may be desirable to rotate the flow cell (or move the camera) so that the entire 360 degrees of angular displacement around the flow cell can be observed. Several different light sources and cameras may be needed. Preferably, the camera and light source cover the spectral range from infrared to blue light (about 900 nm to about 450 nm). The gap region and the liquid flow rate through the flow cell are chosen such that enough light is transmitted through the liquid to enable observation, and the desired shear rates are obtained.

The image processing means 12 can determine the homogeneity of the liquid flowing through the gap region in a variety of ways. In one approach, the image processing means quantifies the extent of homogeneity of the liquid in the gap region to a numerical value. This allows a range of liquid homogeneity values to be displayed for the machine operator. In a second approach, the image processing means renders the information from the camera to a binary answer, e.g., whether the liquid is homogeneous or not homogeneous.

The term homogeneous will now be discussed in the context of a charge generating dispersion, but the discussion herein applies similarly to other types of liquids. As used herein, the term homogeneous refers to a condition of the liquid wherein flocculation has not proceeded to the extent to which there are discrete solvent rich areas separated from pigment rich areas, which are detectable by the image processing means. Likewise, the phrase not homogeneous indicates that the flowing dispersion has flocculated into solvent rich areas distinctly separated from pigment rich areas, wherein the image processing means may quantify the extent of such separation. To the human eye, solvent rich areas appear light, and pigment rich areas appear dark when the dispersion flow is illuminated with white light as previously described in this specification.

The information from the image processing means can be displayed for a human operator to determine if the liquid has satisfactory homogeneity. In other embodiments, the image processing means can optionally determine whether the homogeneity of the liquid is acceptable and if unacceptable can shut off the flow of liquid to the liquid dispensing equipment, and will then send a signal for a human operator.

The image processing means preferably comprises a cable, an interface circuit board, a personal computer, image acquisition software, and image analysis software. The cable connects the camera to the interface circuit board, which is installed in the personal computer. The software programs enable the images that are provided to the interface circuit board to be acquired in digital form, and subsequently analyzed by the computer.

In embodiments, the camera and image processing means extracts and digitizes the images of the liquid in the gap region using for instance a CCI) sensor. Dependent on lighting conditions and noise signal reduction techniques, the CCD sensor detects differences in contrast levels. Dark ground lighting techniques can be used to enable the CCD sensor to acquire optimized sensitivity at each measuring time. When defects are illuminated, changes in reflective angle distinguishes defect type and formation. Defect characterization (e.g., shape and size) are then collected, judged, and classified (e.g., accept/reject).

Figure 2:
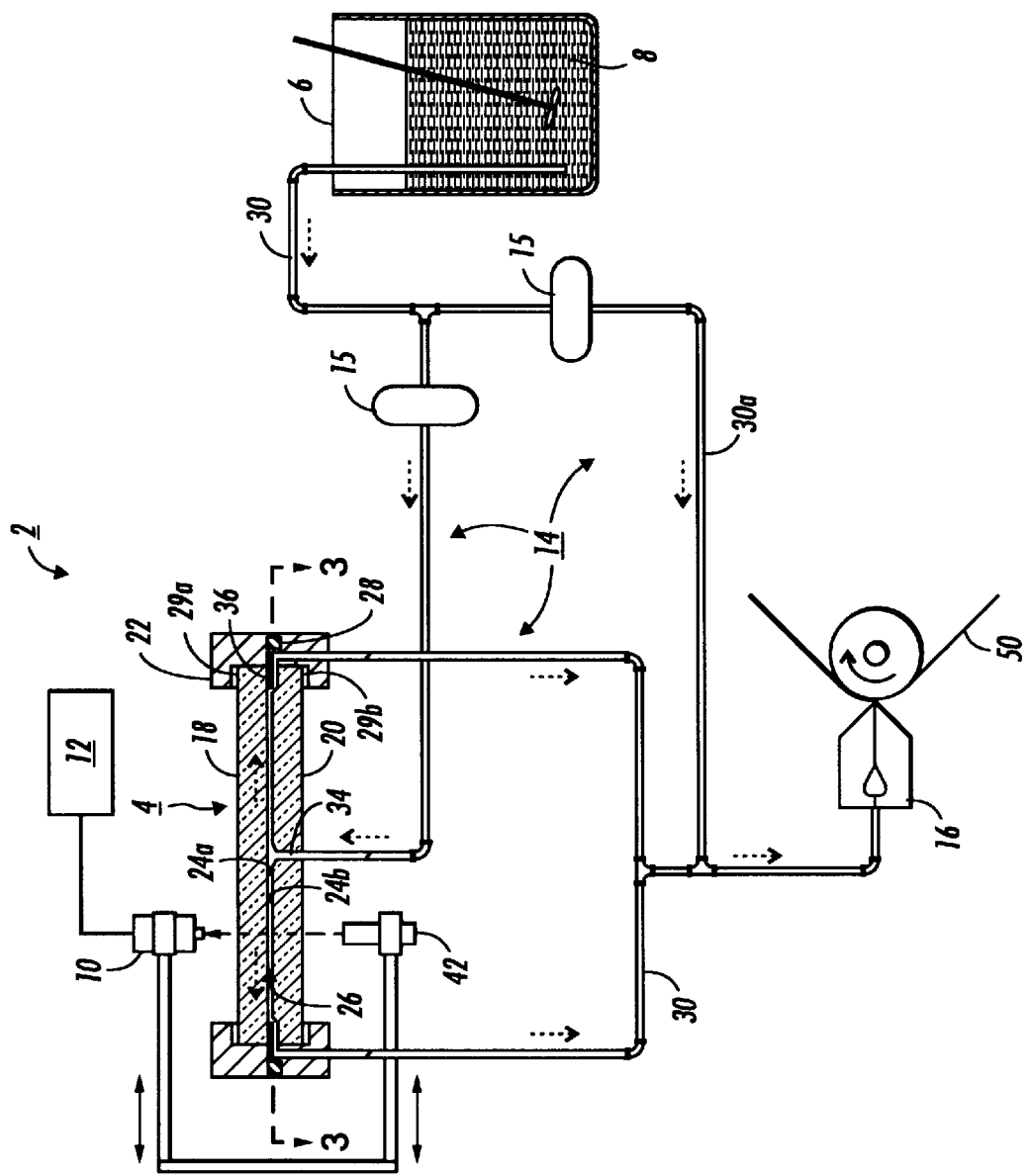
FIG. 2 is a simplified elevational drawing of another embodiment of the present manufacturing system.

The liquid dispensing equipment 16 as depicted in FIGS. 1–2 is a substrate coater apparatus, particularly a web coater composed of a coating die where a uniform layer of the liquid is dispensed by the coating die onto a moving web substrate 50. Subsequent processing stations can include a web drying station and a station for performing on-line thickness measurements. Alternatively, the liquid dispensing equipment may comprise a dip coating apparatus, a spray coating apparatus, a paint manufacturing apparatus, a fermentation apparatus, an emulsion apparatus, a coal slurry apparatus and the like.

Figure 4:
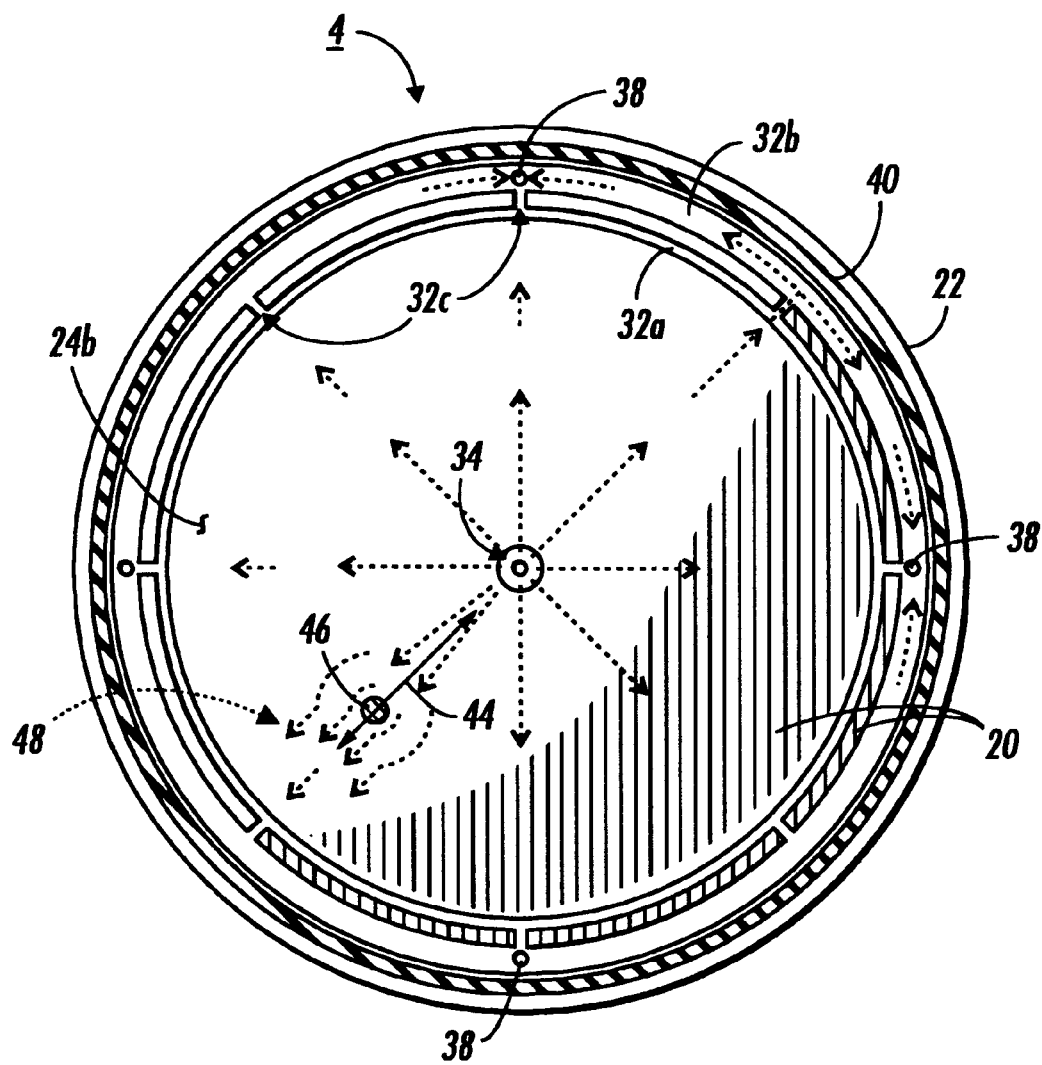
FIG. 4 is a simplified, plan view of the bottom half of the flow cell used in FIG. 1 further including an obstruction.

FIG. 4 illustrates another embodiment where an obstruction 46 is disposed in the gap region to partially obstruct the flow of the liquid, wherein the liquid flows around the obstruction to form a wake region 48, and the camera is positioned to view the wake region of the liquid. A row 44 shows the radially oriented image scanning pathway of the camera from about the center of the flow cell past the obstruction to the edge of the flow cell. The obstruction 46 may be circular, elliptical, rectangular, triangular, or square in shape. The major dimension of the obstruction is preferably between 1 mm and 8 mm.

In operation of the manufacturing system shown in FIGS. 1–4, the liquid is pumped from the vessel into the center of the gap region at for example a constant rate. The fluid flows through the gap region radially outward through the flow cell, and exits through the channels and outlet ports at the perimeter of the flow cell. Based on information from the camera, the image processing means determines the homogeneity of the liquid flowing through the gap region. The liquid which has passed from the flow cell is conveyed to the liquid dispensing equipment. In one embodiment of the manufacturing system as illustrated in FIG. 1, all the liquid from the vessel must first pass through the flow cell before being conveyed to the liquid dispensing equipment. FIG. 2 illustrates another embodiment where a portion of the liquid bypasses the cell flow and is conveyed from the vessel directly to the liquid dispensing equipment via tubing 30a.

Figure 5:
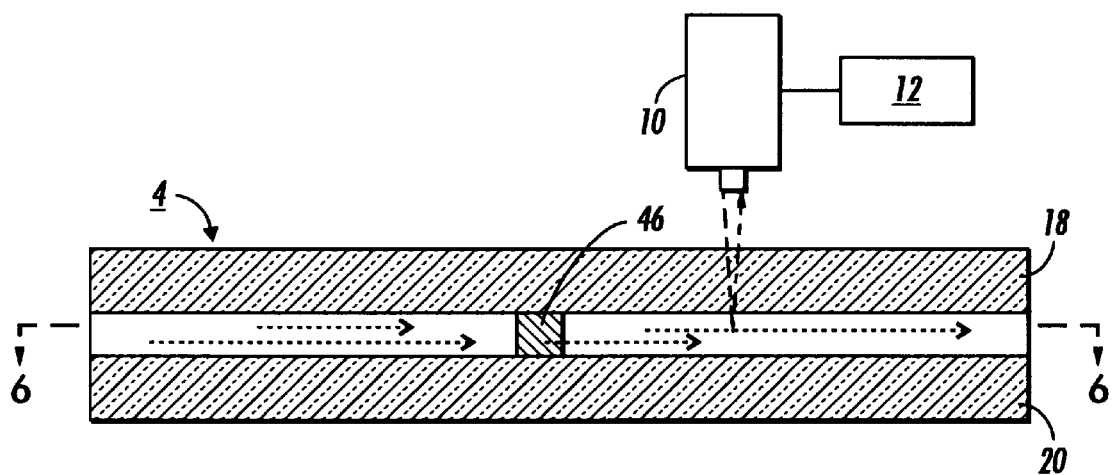
FIG. 5 is a simplified, elevational view of still another embodiment of the flow cell.
Figure 6:
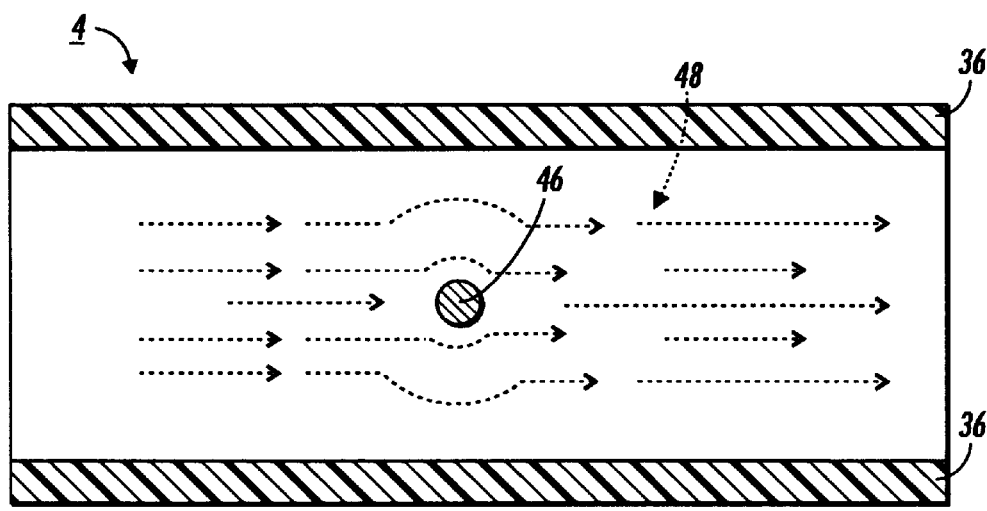
FIG. 6 is a simplified, top view of the bottom half of the flow cell depicted in FIG. 5.

FIGS. 5–6 illustrate another embodiment of the flow cell where the first member 18, the second member 20, and the gap region 26 are rectangularly shaped. In addition, there is an optional obstruction 46 at about the center of the gap region to partially obstruct the flow of the liquid, wherein the liquid flows around the obstruction to form a wake region 48, and the camera 10 is positioned to view the wake region. Shims 36 are present to determine the width of the gap region. The liquid delivery system directs the liquid to flow in the gap region in a linear orientation. In this embodiment, the camera can be stationary. Operation of a manufacturing system incorporating the flow cell of FIGS. 5–6 proceeds in a similar manner as that described herein for FIGS. 1–4.

The present manufacturing system allows an on-line observation and simulation of flow conditions and shear rates which occur for example in the die coating and dip coating processes used to manufacture web and drum organic photoreceptors, respectively. As flow occurs radially outward from the center of a circular flow cell to the perimeter, a Newtonian fluid would be subject to decreasing wall shear as it slows down due to mass conservation according to the equation (the first member and the second member are referred as disks below):

$$j_w = \frac{dv_r}{dz}\bigg|_{z=B} = \frac{-(P_1 - P_2)B}{\mu ln(r_2/r_1)} \cdot \frac{1}{r}$$

$j_w$=the shear rate at the flow cell wall at radial position r, $sec^{-1}$;

$\mu$=the fluid viscosity, $g\ cm^{-1}\ sec^{-1}$;

B=one half of the separation (gap region) between the two disks, cm;

r=radial position within the flow cell, cm;

$r_1$=the radius of the disks near the center liquid inlet port, cm;

$P_1$=the fluid pressure at radius $r_1$, $g\ cm^{-1}\ sec^{-2}$;

$r_2$=the radius of the disks near the outer liquid outlet ports (outlet channels), cm;

$P_2$=the fluid pressure at radius $r_2$, $g\ cm^{-1}\ sec^{-2}$.

It is apparent that for a Newtonian fluid, the shear rate in the flow cell varies inversely with radial position r. Even for a non-Newtonian fluid, the flow cell can subject the fluid to a controlled range of shear rates in a single experiment without the need to vary either the size of the gap region or the liquid flow rate through the flow cell. In practice, conditions of flow rate and gap region are chosen which produce shear rates comparable to those that occur in the coating process of interest. The flow through the flow cell can be in either direction. If it is desired to study the behavior of the liquid during a transition from low shear to high shear, the liquid flow would be from the perimeter to the center. Conversely, to study a transition from high shear to low shear, the liquid flow would be from the center to the perimeter of the flow cell.

To observe and record the resulting flow, the camera and light source are scanned radially outward from the center of the flow cell to the perimeter of the flow cell. In the system shown in FIG. 1, the radial displacement which can be recorded by the camera varies from r equals about 0.8 cm to r equals about 11.0 cm. At steady state operation, therefore, a single scan of the camera can record approximately a thirteen fold decrease in shear rate from center to perimeter. This has been demonstrated to be sufficient to observe the transition from a well-dispersed homogeneous flow to a two phase flocculated flow, as will be seen in the examples below.

The following parameters are illustrative of the present invention. The flow cell may have a diameter of about 15 cm. The gap region may range for example from about 0.001 cm to 0.03 cm. Preferably, the gap region may range from about 25 to about 100 micrometers. The liquid flow rate may range for instance from about 5 to about 800 cc/min. The viscosity of the liquid may range from about 1 to about 500 cp, while limiting pressure drop rate through the flow cell to a maximum for example of about 100 psi. For any given experimental setup, the minimum and maximum shear rates which will be observable by the camera along the radial direction may differ by for instance a factor of between about 10× and 20×, i.e., observable shear rate can vary by more than an order of magnitude.

Figure 7:
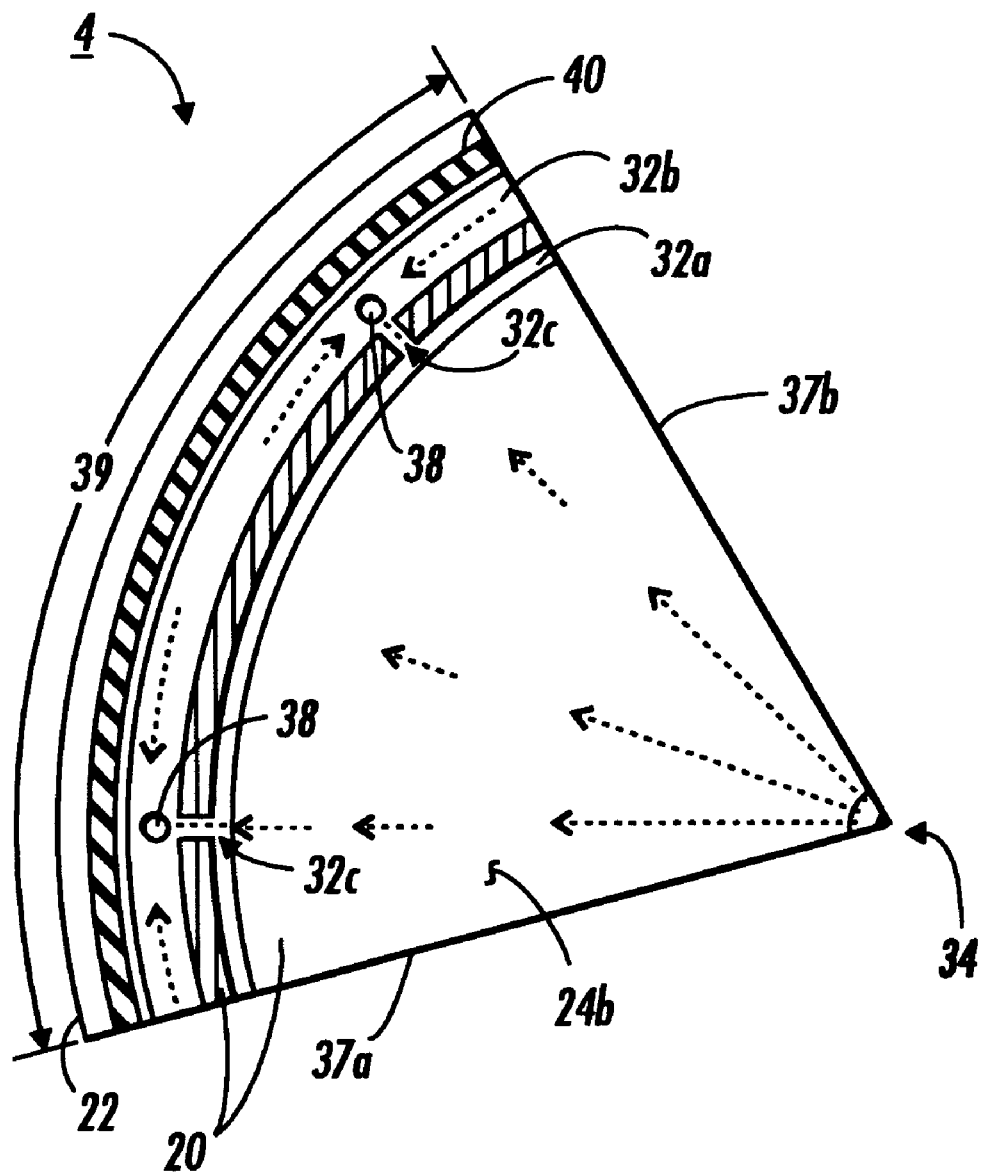
FIG. 7 is a simplified, plan view of the bottom half of yet another embodiment of the flow cell.

In an alternative embodiment, the flow cell may be sectorial in shape resembling for example a sector from the flow cell depicted in FIG. 3. In particular, referring to FIG. 7, the flow cell 4 is defined by the liquid inlet port 34, radii 37a and 37b, and arc 39. In this embodiment, liquid is delivered to the flow cell through inlet port 34, which is located at the apex of the sector. Fluid flow within the flow cell would occur radially outward in a fan shaped pattern toward arc 39. At any point in the sectorial flow cell that is greater than five gap thicknesses distant from the radial boundaries of the flow cell, the fluid flow may be approximated by the same analysis as presented for the circular flow cell discussed herein.

The advantages of a sectorial flow cell would be smaller physical size and lower fabrication costs. A sectorial flow cell would comprise an arc with an included angle preferably between 30 and 120 degrees.

In embodiments of the present invention, the manufacturing system incorporates the flow cell with automatic vision inspection apparatus, i.e., the camera and the image processing means to continuously monitor the liquid which can be for instance a coating solution. The coating solution is continuously pumped from the vessel to the liquid dispensing equipment which can include a dip coating tank. Solution overflow at the dip coating tank is returned to the vessel which can be a recirculation tank. The flow cell can be added as a recirculation loop from the recirculation tank. An automatic vision inspection ("AVI") apparatus could then monitor the visual characteristics of the liquid as it is passed through the flow cell. The AVI apparatus would be able to detect the formation of for example streaks and blotches as the liquid aged. AVI data could be quantified and control limits can be set up indicating to change the liquid before unacceptable coating defects start to appear. This manufacturing system would increase yield by preventing or minimizing rejects due to poor dispersions.

The liquid can be a dispersion, suspension, or emulsion. The liquid is a multi-phase liquid wherein the phrase multi-phase refers to the presence of two, three, or more different components. For example, the liquid may be a dispersion of magnetic particles, a photographic emulsion, a paint, a lacquer, a pigmented ink, a fermentation broth, a latex suspension, a pigment slurry, a coal-water slurry, a pigmented polymer melt, and the like.

In preferred embodiments, the liquid is a coating solution composed of components for the charge transport layer and/or the charge generating layer, such components and amounts thereof being illustrated for instance in U.S. Pat. No. 4,265,990, U.S. Pat. No. 4,390,611, U.S. Pat. No. 4,551,404, U.S. Pat. No. 4,588,667, U.S. Pat. No. 4,596,754, and U.S. Pat. No. 4,797,337, the disclosures of which are totally incorporated by reference. In embodiments, the coating solution may be formed by dispersing a charge generating material selected from azo pigments such as Sudan Red, Dian Blue, Janus Green B, and the like; quinone pigments such as Algol Yellow, Pyrene Quinone, Indanthrene Brilliant Violet RRP, and the like; quinocyanine pigments; perylene pigments; indigo pigments such as indigo, thioindigo, and the like; bisbenzoimidazole pigments such as Indofast Orange toner, and the like; phthalocyanine pigments such as copper phthalocyanine, aluminochlorophthalocyanine, and the like; quinacridone pigments; or azulene compounds in a binder resin such as polyester, polystyrene, polyvinyl butyral, polyvinyl pyrrolidone, methyl cellulose, polyacrylates, cellulose esters, and the like. In embodiments, the coating solution may be formed by dissolving a charge transport material selected from compounds having in the main chain or the side chain a polycyclic aromatic ring such as anthracene, pyrene, phenanthrene, coronene, and the like, or a nitrogen-containing hetero ring such as indole, carbazole, oxazole, isoxazole, thiazole, imidazole, pyrazole, oxadiazole, pyrazoline, thiadiazole, triazole, and the like, and hydrazone compounds in a resin having a film-forming property. Such resins may include polycarbonate, polymethacrylates, polyarylate, polystyrene, polyester, polysulfone, styrene-acrylonitrile copolymer, styrene-methyl methacrylate copolymer, and the like. The coating solution may also contain an organic solvent such as one or more of the following: tetrahydrofuran, monochlorobenzene, toluene, butyl acetate, and cyclohexanone.

The liquid is deposited on a substrate during for instance the fabrication of a photoreceptor, where the substrate can be in the form of a belt, a web, a tube, a seamless sleeve, or a drum.

The invention will now be described in detail with respect to specific preferred embodiments thereof, it being understood that these examples are intended to be illustrative only and the invention is not intended to be limited to the materials, conditions, or process parameters recited herein. All percentages and parts are by weight unless otherwise indicated.

EXAMPLES

A manufacturing system as described in FIGS. 1 and 3 was used to determine the homogeneity of a charge generating solution, dispersion A. In order to observe the dispersion flow behavior in the flow cell, a Sony 3-CCD color camera equipped with a Navitar long distance zoom microscope was used. The camera was mounted, pointing downward, on a motorized precision slide via a modified photographic copy stand. An application was programmed using the Labview visual programming software on a notebook computer to move the camera from the cell axis to the circumference according to a prescribed speed versus radial position profile. The Newtonian $r^{-2}$ dependence of the average flow velocity was programmed in the application in order to follow a fluid element in its travel towards the flow cell's circumference. Because the rheology of the dispersion fits more closely to a Herschel-Buckley model (yield stress with shear-thinning power law behavior after yield) than to the Newtonian model, two features where programmed in the camera motion algorithm in order to modify the camera velocity from the Newtonian profile on the fly: A speed factor knob, and a "zip" button to either speed up or slow down the camera temporarily in order to follow a different fluid element. The camera radial position and speed were superimposed in a corner of the flow field video stream. A fiber optic light bundle was placed under the cell, coaxial with the camera, and mounted on the same motorized slide, to supply the high intensity back-lighting needed to best visualize the breakdown of the very dark dispersion. Coaxial and oblique lighting from the camera side where also tried but found not satisfactory. The camera field of view was varied in the range 0.7–10 mm. The video stream from the camera was recorded on S-VHS tape using a Panasonic AG-DS850 VTR. Most of the experiments were performed with two cell gap values: 25.4 micrometers (0.001 inch) and 127 micrometers (0.005 inch), but the best images were obtained with the smaller gap due to the darkness of the dispersion. Several dispersions where tested in the apparatus. Along with the circular flow cell, a rectangular flow cell was designed and built to perform studies at uniform shear rate and to image the flow patterns at the advancing meniscus during cell filling.

Although considerable qualitative evidence was obtained using both flow cells, it was necessary to continue the study to obtain reproducible measurements of the onset of flocculation. For this purpose, images from the videos recorded with the circular flow cell were digitized using a Data Translation DT3155 monochrome frame grabber board with image acquisition driver software in a Windows NT4.0 computer and analyzed with Vision Blox software. Images were made binary by thresholding, then blob analysis was performed to extract size and shape information about the brighter features. In one experiment, using dispersion A, a separation gap of 25.4 micrometers (0.001 inch) was chosen, with a flow rate of 0.00365 cm$^3$/sec. The camera and light source were scanned from r equals 0.8 cm to r equals 11.0 cm. As the dispersion traveled outward to regions of lower shear, it reached a point where the pigment started to segregate and brighter, pigment-poor regions appeared. These regions grew in size until a significant fraction of the image was free from pigment (just the dispersant). An approximate (Newtonian) average shear stress $j_{avg}$ was calculated as a function of the radial position wherein $$j_{avg} = \frac{Q}{2\pi B^2} \cdot \frac{1}{r}$$

according to the above formula. The average area (in arbitrary units) of the bright features in each image was plotted as a function of the average shear stress. The plot and related flow images showed that the onset of flocculation was quite sharp. Although segregated, in dispersion A, both pigment-rich and pigment-free regions continued to move. Another charge generating solution, dispersion B, showed an even more dramatic transition: Stationary pigment "islands" developed, while "rivers" or "channels" of pigment-poor liquid flowed around them.

Other modifications of the present invention may occur to those skilled in the art based upon a reading of the present disclosure and these modifications are intended to be included within the scope of the present invention.

We claim:

1. A manufacturing system comprising:
   (a) a vessel for holding a liquid;
   (b) a first member and a second member, each having a flat surface, wherein the flat surface of the first member faces and is spaced from the flat surface of the second member, thereby defining a gap region between the two flat surfaces, wherein a section of the first member is transparent through the thickness of the first member and wherein a section of the second member is transparent through the thickness of the second member;
   (c) a liquid delivery system connected to the vessel and the gap region which delivers the liquid to the gap region and the liquid flows in the gap region in view of the transparent section of the first member;
   (d) a camera positioned to view through the transparent section of the first member;
   (e) image processing means coupled to the camera for determining the homogeneity of the liquid in the gap region;
   (f) liquid dispensing equipment connected to the liquid delivery system wherein the liquid dispensing equipment is a manufacturing process station; and
   (g) a light source that provides light through the transparent section of the second member to the liquid in the gap region, wherein the camera and the light source are disposed on opposite sides of the flat surface of the first member, whereby the camera views through the liquid in the gap region in transmission.

2. The system of claim 1, wherein the liquid dispensing equipment is a substrate coater apparatus.

3. The system of claim 1, further comprising the liquid and wherein the liquid includes a solvent, a binder resin, and an ingredient selected from a charge generating material and a charge transport material.

4. The system of claim 1, wherein the first member is transparent along the entire length of the first member and through the thickness of the first member.

5. The system of claim 1, wherein the image processing means quantifies the extent of homogeneity of the liquid in the gap region to a numerical value.

6. The system of claim 1, wherein the first member, the second member, and the gap region are circular, and the liquid delivery system includes a single liquid inlet port positioned at the center of the gap region, wherein the liquid flows in the gap region in a radial pattern.

7. The system of claim 1, wherein the first member, the second member, and the gap region are sectorial, and the liquid delivery system includes a single liquid inlet port positioned at the apex of the gap region, wherein the liquid flows in the gap region in a radial pattern.

8. The system of claim 1, wherein the first member, the second member, and the gap region are rectangularly shaped, and the liquid delivery system directs the liquid to flow in the gap region in a linear orientation.

9. The system of claim 1, wherein the flat surface of the first member and the flat surface of the second member are ground flat to within about 632 nanometers.

10. The system of claim 1, further comprising an obstruction disposed in the gap region to partially obstruct the flow of the liquid, wherein the liquid flows around the obstruction to form a wake region, and the camera is positioned to view the wake region of the liquid.

* * * * *